United States Patent [19]

Idel

[11] 4,212,774

[45] Jul. 15, 1980

[54] RECOVERY OF HIGH-QUALITY POLYCARBONATE FROM POLYCARBONATE SCRAP

[76] Inventor: Karsten Idel, c/o Bayer AG, Krefeld-Uerdingen, Fed. Rep. of Germany, D 4150

[21] Appl. No.: 34,840

[22] Filed: Apr. 30, 1979

Related U.S. Application Data

[63] Continuation of Ser. No. 930,612, Aug. 3, 1978, abandoned.

[30] Foreign Application Priority Data

Aug. 20, 1977 [DE] Fed. Rep. of Germany ....... 2737693

[51] Int. Cl.$^2$ .............................................. C08J 11/04
[52] U.S. Cl. .................................... 260/2.3; 528/196; 528/488; 528/489; 528/491
[58] Field of Search ................. 260/2.3; 528/196, 488, 528/489, 491

[56] References Cited

U.S. PATENT DOCUMENTS

| | | | |
|---|---|---|---|
| 3,008,980 | 11/1961 | Katzschmann | 260/2.3 X |
| 3,427,370 | 2/1969 | Schnell et al. | 264/37 |
| 3,728,287 | 4/1973 | Burmaster | 260/2.3 |
| 4,040,991 | 8/1977 | Wiggins et al. | 260/2.5 BD |
| 4,051,212 | 9/1977 | Grigab et al. | 264/102 |
| 4,136,967 | 1/1979 | Grigab et al. | 366/82 |

FOREIGN PATENT DOCUMENTS

| | | |
|---|---|---|
| 910593 | 5/1954 | Fed. Rep. of Germany . |
| 1234026 | 2/1967 | Fed. Rep. of Germany . |
| 2442387 | 3/1976 | Fed. Rep. of Germany . |
| 2283766 | 2/1976 | France . |

OTHER PUBLICATIONS

Die Makromoleculare Chemie, Band 65, (1963), pp. 252–253.

*Primary Examiner*—Richard B. Turer

[57] ABSTRACT

The present invention relates to a process for the recovery of aromatic, high-molecular weight, thermoplastic polycarbonates from polycarbonate scrap, it being possible for the polycarbonate scrap to be either in the pure form as transparent naturally-occurring material, or mixed together with organic and, especially, inorganic dyestuffs and/or other additives, or in the form of a blend with other thermoplastic materials.

7 Claims, No Drawings

RECOVERY OF HIGH-QUALITY POLYCARBONATE FROM POLYCARBONATE SCRAP

This is a continuation, of application Ser. No. 930,612 filed Aug. 3, 1978, now abandoned.

BACKGROUND OF THE INVENTION

Because of the increasing shortage of raw material resources and the raw material price increases resulting therefrom, processes for working up plastic consumer articles which are no longer useful, in the sense of recovery either of starting substances or the original plastic directly, are becoming more and more important.

Thus, in German Democratic Republic Patent Specification Nos. 45,575, 46,282, 45,599, 45,600 and 46,353, E. Bullack describes a process for the working up of polycarbonates, in particular with regard to the isolation of 4,4'-dihydroxy-diaryl-alkanes as starting substances for polycarbonate syntheses.

According to German Democratic Republic Patent Specification Nos. 45,575, 46,282 and 45,599, the 4,4'-dihydroxy-diaryl-alkanes are obtained, after purification processes which in some cases are expensive, via cleavage by means of alcohols, acid anhydrides or small amounts of basic catalysts. According to Patent Specification Nos. 45,600 and 46,353, the cleavage is achieved by adding phenols or diaryl carbonates in the presence of metal oxide catalysts at temperatures above 180° C. There is the danger of side reactions at these temperatures, especially if metal oxide catalysts are present, and extensive purification operations are necessary in order to isolate clean starting substances.

SUMMARY OF THE INVENTION

The present invention relates to a process for the recovery of aromatic, high-molecular weight, thermoplastic polycarbonates from polycarbonate scrap, which is characterized in that the polycarbonate strap is saponified in bulk or in solution at temperatures between about 25° C. and 220° C., the non-saponified constituents are then separated off and the saponification mixture is then phosgenated and subjected to polycondensation by the two-phase boundary polycondensation methods, without further purification steps and treatment steps.

DETAILED DESCRIPTION OF THE INVENTION

It has now been found, surprisingly, that it is possible to gently saponify polycarbonates, either in the pure or colored form or in the form of polymer blends, in a one-pot reaction which proceeds smoothly, and, if appropriate after filtering off additives, dyestuffs and the like constituents of the blend, then to phosgenate the products again in a smooth one-pot reaction in the same reaction media to give high-molecular weight, thermoplastic and soluble polycarbonates. Polycarbonates have thus been cleaved without adding catalysts which are troublesome later and under mild conditions with respect to heat, and the reaction mixture which remains after the cleavage can be directly reacted again, without intermediate purification, by the phase boundary process, in order to synthesize polycarbonates.

After adding a water-immiscible solvent which is customary in the phase boundary condensation of polycarbonates, such as, for example, methylene chloride or chlorobenzene, the condensation reaction can be carried out directly, by passing in phosgene, without any intermediate purification. The pH value of the alkaline phase should be kept between about 9 and 14 during this procedure, depending on the nature of the diphenol. Tertiary amines, such as, for example, triethylamine, tributylamine or N-alkylpiperidine, or ammonium, sulphonium, phosphonium or arsonium compounds or also nitrogen-hetaryls, such as, for example, pyridine, are usually added before, and especially after, the phosgenation.

After the saponification step, the monohydric phenols present in scrap polycarbonates at the chain ends are found as cleavage products in the alkaline reaction medium and are again incorporated completely as chain stoppers during or after the phosgenation, so that the resynthesized polycarbonates attain the same solution viscosity as the polycarbonate scrap reacted as the starting material. If other soluble viscosities are to be established, an additional amount of free bisphenol can be metered in for a higher desired solution viscosity, and an additional amount of monohydric phenol can be metered in for a lower solution viscosity.

Cocondensed compounds with more than two functional groups capable of undergoing condensation, such as, for example, trisphenols or tetraphenols, which are incorporated as branching agents into polycarbonates, are also incorporated again completely during the resynthesis of the polycarbonates. A change in the branching agent concentration in the recovered polycarbonate is again made possible by adding an additional amount of branching agent or of free bisphenol to the reaction medium before the phosgenation.

Polycarbonate strap is to be understood as all polycarbonate plastic articles which can no longer be used, and also the residues, scrap, trimmings and the like obtained during the preparation and shaping of the polycarbonate plastic.

The polycarbonate scrap suitable for reuse results from aromatic homopolycarbonates and copolycarbonates, which are based, for example, on one or more of the following diphenols: hydroquinone, resorcinol, dihydroxydiphenyls, bis-(hydroxyphenyl)-alkanes, bis-(hydroxyphenyl)-cycloalkanes, bis-(hydroxyphenyl)-sulphides, bis-(hydroxyphenyl)ethers, bis-(hydroxyphenyl) ketones, bis-(hydroxyphenyl) sulphoxides, bis-(hydroxyphenyl) sulphones, $\alpha,\alpha'$-bis-(hydroxyphenyl)-diisopropylbenzenes and, for example, their nuclear-halogenated compounds. These and further suitable diphenols are described, for example, in U.S. Pat. No. 3,028,365, incorporated herein by reference, and in the monograph "H. Schnell, Chemistry and Physics of Polycarbonates, Interscience Publishers, New York, 1964".

Examples of preferred diphenols are: 4,4'-dihydroxydiphenyl, 2,2-bis-(4-hydroxyphenyl)-propane (bisphenol A), 2,4-bis-(4-hydroxyphenyl)-2-methylbutane, 1,1-bis-(4-hydroxyphenyl)-cyclohexane, $\alpha,\alpha'$-bis-(4-hydroxyphenyl)-p-diisopropylbenzene, 2,2-bis-(3-chloro-4-hydroxyphenyl)-propane, 2,2-bis-(3,5-dichloro-4-hydroxyphenyl)-propane and 2,2-bis-(3,5-dibromo-4-hydroxyphenyl)-propane.

The aromatic polycarbonates which can be reused as polycarbonate scrap can also be branched by incorporating small amounts, preferably amounts between about 0.05 and 2.0 mol % (relative to diphenols employed), of compounds which are trifunctional or more than trifunctional, in particular those with three or more than three phenolic hydroxyl groups, for example by incorporating phloroglucinol, 1,3,5-tri-(4-hydroxyphenyl)-benzene, 1,1,1-tri-(4-hydroxyphenyl)-ethane or 1,4-bis-(4,4'-dihydroxytriphenyl-methyl)benzene.

As a rule, the aromatic polycarbonates which can be reused as polycarbonate scrap have average weight average molecular weights Mw of about 10,000 to over 200,000, preferably of about 20,000 to 80,000, determined by measurements of the relative viscosity in $CH_2Cl_2$ at 25° C. and at a concentration of 0.5% by weight.

The molecular weights of the polycarbonates can be regulated in the customary manner, for example by incorporating phenol, tribromophenol or p-tert.-butylphenol.

The polycarbonates which can be reused from polycarbonate scrap can also be in the form of mixtures of different polycarbonates, for example mixed with proportions of low-molecular polycarbonates, or can also be in the form of polymer blends, for example with polymers or copolymers based on styrene, styrene/acrylonitrile, acrylonitrile/butadiene/styrene or butadiene rubber.

The polycarbonate scrap is saponified in bulk or in solution, the solvents used being the customary solvents which are suitable for the preparation of polycarbonates by the two-phase boundary process, such as methylene chloride or chlorobenzene.

The saponification is carried out in a neutral, but preferably alkaline, aqueous reaction medium, the saponification in bulk being effected heterogeneously and the saponification in solution being effected at the boundary of the two-phase system, the latter proceeding more favourably and rapidly. With respect to the aqueous reaction medium there are preferably used between 25 and 100 moles of water per mol of structural polycarbonate unit to be saponified.

Examples of basic saponification agents which can be used are sodium hydroxide, potassium hydroxide and calcium oxide, preferably sodium hydroxide.

The saponification is carried out at temperatures between about 25° and 220° C., optionally applying excess pressure, preferably up to about 100 atmospheres.

The amount of basic saponification agents is between about 0.01 and 15 times the molar amount, relative to the mols of aromatic hihydroxy compound formed; the pH value of the saponification medium is between about 9 and 14; and the saponification time is between about 0.5 and a maximum of 20 hours, depending on the steric shielding of the carbonate structure.

Phosphites or phosphines can additionally be added as catalysts.

If the polycarbonate scrap contains unsaponifiable constituents, such as lubricants, stabilizers, pigments, dyestuffs and fillers, such as glass powder, quartz products, graphite, molybdenum sulphide, metal powders, powders of higher-melting plastics, such as p-lytetraethylene powder, natural fibers, such as asbestos, and furthermore glass fibers of the most diverse nature, metal filaments and the like, after the saponification has been carried out, these are separated off in a known manner, for example by filtration.

The single-phase or two-phase solutions resulting after the saponification of the polycarbonate scrap can be employed directly for the preparation of polycarbonates by the phase boundary process, the customary polycarbonate solvents, such as methylene chloride or chlorobenzene, being appropriately added and the pH value of the aqueous solution being adjusted to between about 9 and 14, depending on the requirement.

The subsequent phosgenation is usually carried out at room temperature, an amount of phosgene of about 1 to 3 mols, relative to 1 mol of diphenol, preferably being employed.

The phosgenation time is a maximum of about 1 hour.

Tertiary amines or other polycondensation catalysts are added in amounts between about 0.01 to 10 mol %, relative to the mols of diphenols, before, or especially after, the phosgenation.

The polycondensation reaction is then carried out in the customary manner at temperatures between about 20° and 40° C. for a period of about 1-5 hours, depending on the diphenol employed.

The polycarbonate solutions obtained are worked up in the customary manner and the polycarbonate is isolated in the customary manner.

EXAMPLES

EXAMPLE 1

25.4 g of a polycarbonate obtained from 2,2-bis-(4-hydroxyphenyl)-propane and having a solution viscosity $\eta_{rel}=1.288$ (measured on a solution of 0.5 g of polycarbonate in 100 ml of methylene chloride) are added, in the form of granules, to 80 ml of 15 N sodium hydroxide solution. The reaction mixture is heated to 100° C. for 4 hours. In this time, complete cleavage of the polycarbonate down to the monomer unit bisphenol A is achieved. If 500 ml of distilled water are added to the resulting suspension, a clear alkaline solution of bisphenol A is obtained which, after adding 500 ml of methylene chloride, can be phosgenated by the customary phase boundary condensation methods.

For this, 15 g of phosgene are passed in at 25° C. in the course of 1 hour, the pH value being adjusted to 13-14, and, after adding 1.5 mol of a 4% strength aqueous triethylamine solution, the condensation reaction is then carried out for a further 1 hour. The organic phase is separated off and washed twice with 2% strength phosphoric acid and then with distilled water until free from electrolytes. After evaporating off the solvent, 24 g of polycarbonate are obtained with a $\theta_{rel}=1.295$. The recycled polycarbonate exhibits mechanical and rheological properties which are equally as good as those of the starting material.

EXAMPLE 2

25.4 g of the polycarbonate of Example 1, obtained from 2,2-bis-(4-hydroxyphenyl)-propane are added, in the form of granules, to 30 ml of 15 N sodium hydroxide solution. 2.5 g (10% by weight) of triphenyl phosphite are also additionally added, and saponification is then carried out at 100° C. according to Example 1. By adding the phosphite, the time until saponification is complete is shortened to 2 hours 45 minutes. Thereafter, phosgenation is carried out at the phase boundary analogously to Example 1. The polycarbonate recovered has a solution viscosity $\eta_{rel}=1.297$ and, after precipitation from the methylene chloride solution by means of methanol, exhibits no difference from the starting material with respect to the mechanical and rheological properties.

EXAMPLE 3

25.4 g of the polycarbonate according to Example 1, obtained from 2,2-bis-(4-hydroxyphenyl)-propane are dissolved in 300 ml of chlorobenzene, and 80 ml of 15 N sodium hydroxide solution are added as the alkaline phase. The mixture was brought to 100° C. and the content of polycarbonate still not saponified in the organic phase was examined at short intervals of time. The cleavage had completely ended after 60 minutes, and the phase boundary mixture could be phosgenated directly analogously to Example 1, after adding 350 ml of water, and the phosgenation mixture then subsequently worked up. 23.5 g of a polycarbonate are obtained with a $\eta_{rel}$ of 1.315 and a similar pattern of properties to the starting material.

By adding 450 mg of p-tert.-butylphenol to the saponification mixture as an additional chain stopper, the solution viscosity $\eta_{rel}=1.282$ can be obtained after the phosgenation and condensation reaction.

EXAMPLE 4

The saponification time and amount of the base employed are directly related. As this example shows, the amount of sodium hydroxide employed can be reduced at the expense of extended saponification times. The saponification was carried out at the phase boundary: 25.4 g of the polycarbonate of Example 1 were dissolved in 300 ml of chlorobenzene and varying amounts of 15 N sodium hydroxide solution were added. In each case the time until the saponification of the polycarbonate was complete was measured:

25.4 g of the polycarbonate from Example 1 in 300 ml of chlorobenzene and 80 ml of 15 N NaOh results in a saponification time of 55 minutes; in 300 ml of chlorobenzene and 63 ml of 15 N NaOH in a saponification time of 70 minutes; in 300 ml of chlorobenzene and 46 ml of 15 N NaOH in a saponification time of 120 minutes and in 300 ml of chlorobenzene and 33 ml of 15 N NaOH in a saponification time of 260 minutes.

EXAMPLE 5

The saponification can also be carried out under pressure. 101.6 g of the polycarbonate of Example 1, 400 ml of distilled water and 2.26 g of 45% strength sodium hydroxide solution are heated to 210° C. under pressure of 50 bars in an autoclave in the course of 1 hour and kept under these conditions for 2 hours. 840 g of 6.2% strength sodium hydroxide solution and 1,500 ml of methylene chloride are added to the resulting mixture. 60 g of phosgene are passed in during the course of 1 hour while maintaining a pH value of 13–14, and, after adding 6 ml of 4% strength aqueous triethylamine, the condensation reaction is then carried out for 1 hour. The reaction mixture is worked up according to Example 1. Since it is probable that small amounts of monofunctional monomers are split off during the saponification under pressure, the solution viscosity of the resulting polycarbonate is $\eta_{rel}=1.212$. A polycarbonate having the desired $\eta_{rel}=1.287$ can be obtained by additionally adding 17 g of bisphenol A to the saponification mixture and correspondingly increasing the proportions of phosgene and triethylamine.

EXAMPLE 6

80 ml of 15 N sodium hydroxide solution are added to 27.9 g of a polycarbonate based on bisphenol A ($\eta_{rel}=1.305$) containing 10% by weight of glass fibers and the mixture is warmed to 100° C. The saponification has ended after 3 hours. 500 ml of distilled water are added to the saponification mixture and the glass fibers which remain are filtered off. 500 ml of methylene chloride are added to the filtrate, and 15 g of phosgene are then added to the mixture analogously to Example 1 and after adding 1.5 ml of a 4% strength aqueous triethylamine solution the mixture is subjected to a condensation reaction. After working up according to Example 1, 10 g of a glass fiber-free polycarbonate are obtained, $\eta_{rel}=1.317$.

The polycarbonate exhibits the same pattern of properties as a polycarbonate of corresponding chain length which has been obtained by customary condensation of bisphenol A and phosgenation by the phase boundary process.

EXAMPLE 7

80 ml of 15 N sodium hydroxide solution are added to 25.4 g of a polycarbonate which is based on bisphenol A, has a solution viscosity $\eta_{rel}=1.367$ and contains 0.2 mol %, relative to the proportions of diphenols of the tetrafunctional branching agent 1,4-bis-(4,4'-dihydroxy-triphenyl-methyl)benzene incorporated therein, and the mixture is kept at 100° C. for 3 hours. Thereafter, 500 ml of distilled H$_2$O are added until a clear solution is formed and 500 ml of methylene chloride are then added. 15 g of phosgene are added to the saponification mixture analogously to Example 1 and the mixture is subjected to a condensation reaction with 1.5 ml of a 4% strength aqueous triethylamine solution. A polycarbonate is obtained by the customary working up methods, which has a solution viscosity $\eta_{rel}=1.375$ and, after cleavage and investigation of the monomer constituents by chromatography, contains 0.2 mol % of the tetrafunctional branching agent.

EXAMPLE 8

36.3 g of a polymer blend which is composed of 30% by weight of an ABS polymer and 70% of a polycarbonate based on bisphenol A ($\eta_{rel}=1.292$) are treated with 120 ml of 15 N sodium hydroxide solution at 100° C. for 10 hours. Thereafter, the mixture is mixed with 500 ml of distilled H$_2$O and the undissolved ABS polymer is filtered off. 500 ml of methylene chloride are then also added to the filtrate and 11 g of phosgene are passed in at room temperature in the course of 1 hour and, after adding 1.5 ml of a 4% strength aqueous triethylamine solution, the condensation reaction is carried out for a further 1 hour. 17 g of the high-molecular, thermoplastic polycarbonate with a solution viscosity $\eta_{rel}=1.305$ are obtained by the customary working up methods.

EXAMPLE 9

80 ml of sodium hydroxide solution are added to 25.4 g of a polycarbonate based on bisphenol A ($\eta_{rel}$ % 1.285), dyed red with 0.35% by weight of cadmium selenide, and the mixture is warmed to 100° C. for 3 hours. Thereafter, the mixture s mixed with 500 ml of distilled H$_2$O and the undissolved colored pigment is filtered off. 500 ml of methylene chloride are added to the clear filtrate and the phase boundary mixture is phosgenated and worked up, as in Example 1. 22 g of a non-dyed, thermoplastic polycarbonate remain with a solution viscosity $\eta_{rel}=1.297$.

EXAMPLE 10

27 g of a copolycarbonate based on bisphenol A and tetrabromo-bisphenol A (5.3% by weight of bromine) ($\eta_{rel}=1.297$) are dissolved in 150 ml of chlorobenzene, and 80 ml of 15 N sodium hydroxide solution are metered in. After 4 hours, the saponification has ended and, after adding 350 ml of methylene chloride and 400 ml of water, a clear phase mixture is obtained. In order to recover the polycarbonate, 15 g of phosgene are passed in at room temperature in the course of 1 hour. At the end of the phosgenation, the solution should have a pH value of abot 11-12. After adding 0.43 ml of triethylamine, the condensation reaction is carried out for a further 1 hour and the mixture is worked up according to Example 1. A bromine-containing polycarbonate results (5.4% of bromine) with a solution viscosity $\eta_{rel}=1.285$ and similar properties to the starting material.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A process for the recovery of aromatic, high molecular weight, thermoplastic polycarbonates from polycarbonate scrap, in which the polycarbonate scrap is saponified in bulk or in solution at temperatures between about 25° C. and 220° C. to form a saponification mixture, the non-saponified constituents are separated off, and the resulting saponification mixture is then phosgenated and subjected to polycondensation by a two phase boundary polycondensation method, without any further purification steps and treatment steps.

2. The process of claim 1, wherein the saponification mixture is branched by incorporating therein from about 0.05 to 2.0 mol %, relative to the diphenols present, of a compound with three or more than three phenolic hydroxyl groups.

3. The process of claim 1, wherein the saponification is carried out at a process of up to about 100 atmospheres.

4. The process of claim 1 wherein the saponification is carried out with between about 0.01 and 15 times the molar amount of basic saponification agent, relative to the mols of diphenols formed, at a pH value between about 9 and 14 and for between about 0.5 and 20 hours.

5. A high molecular weight, thermoplastic polycarbonate produced by the process of claim 1.

6. A process for the recovery of aromatic, high molecular weight, thermoplastic polycarbonates from polycarbonate scrap comprising
 (a) reacting the polycarbonate scrap in bulk or in solution with a saponification agent for from about 0.5 to 20 hours at a temperature of from about 25° to 220° C. and at a pressure of from about 1 to 100 atmospheres wherein
  (i) the saponification agent is selected from the group consisting of sodium hydroxide, potassium hydroxide and calcium oxide,
  (ii) the saponification agent is present in from about 0.01 to 15 mols per mol of aromatic dihydroxy compound formed, and
  (iii) the pH value of the saponification system is from about 9 to 14,
 to form a saponification mixture,
 (b) removing the non-saponified constituents of the polycarbonate scrap from the saponification mixture, and
 (c) subjecting the saponification mixture to phosgenation and to polycondensation by a two phase boundary process to produce aromatic, high molecular weight, thermoplastic polycarbonates.

7. A process for the recovery of aromatic, high molecular weight, thermoplastic polycarbonates from polycarbonate scrap, in which the polycarbonate scrap is saponified in bulk or in solution at temperatures between about 25° C. and 100° C. to form a saponification mixture, the non-saponified constituents are separated off, and the resulting saponification mixture is then phosgenated and subjected to polycondensation by a two-phase boundary polycondensation method, without any further purification steps and treatent steps.

* * * * *